United States Patent [19]

Obert

[11] 4,036,223

[45] July 19, 1977

[54] APPARATUS FOR GENERATING AEROSOLS OF SOLID PARTICLES

[76] Inventor: Jean-Claude Obert, 16, Traverse Saint Pierre, 13100 -Aix-en-Provence, France

[21] Appl. No.: 650,685

[22] Filed: Jan. 20, 1976

[30] Foreign Application Priority Data

Jan. 29, 1975 France ................................ 75.03493

[51] Int. Cl.² ............................................ A61M 15/00
[52] U.S. Cl. .................................... 128/266; 222/193; 128/213; 128/235
[58] Field of Search ............... 128/184, 185, 186, 188, 128/193, 194, 195, 201, 203, 205, 206, 208, 209, 210, 218 A, 218 PA, 265, 266, 142, 235, 236; 222/193, 194

[56] References Cited

U.S. PATENT DOCUMENTS

| 960,523 | 6/1910 | Edde | 128/266 |
|---|---|---|---|
| 2,786,468 | 3/1957 | Singer et al. | 128/218 A |
| 3,478,926 | 11/1969 | Pfeiffer et al. | 222/193 |
| 3,482,782 | 12/1969 | Wilson | 222/193 |
| 3,606,087 | 9/1971 | Ortman | 222/193 |

*Primary Examiner*—Robert W. Michell
*Assistant Examiner*—Henry J. Recla
*Attorney, Agent, or Firm*—Lewis H. Eslinger

[57] ABSTRACT

This invention relates to apparatus for generating aerosols of solid particles, particularly inhalable vaccine, said apparatus being composed of a jet mill or micronizer, comprising, on one of its side walls, cavities which open out into the chamber of the mill, of syringes containing a determined dose of a pulverulent product which are fitted into said cavities and of means for pushing the plungers of said syringes.

15 Claims, 14 Drawing Figures

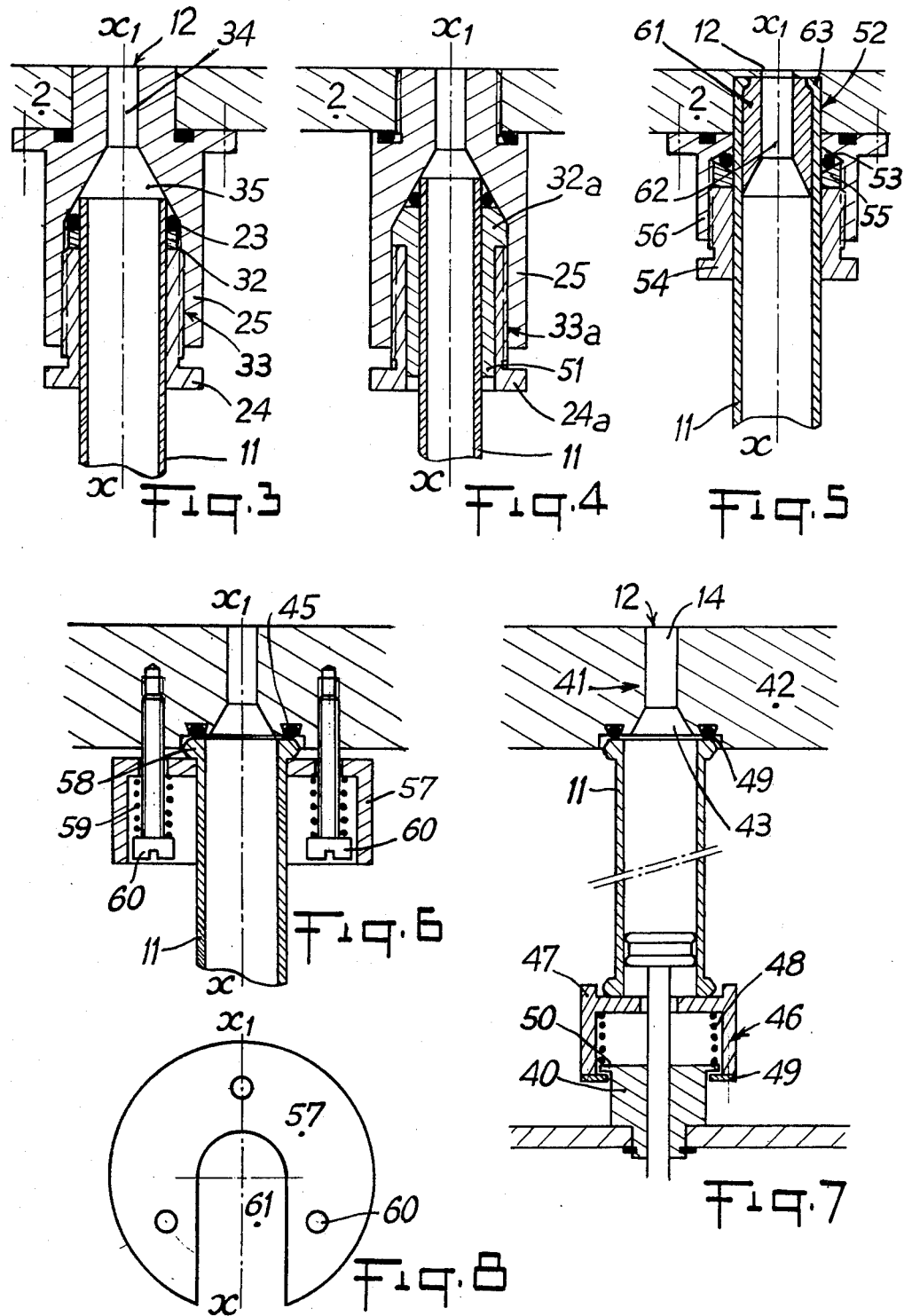

APPARATUS FOR GENERATING AEROSOLS OF SOLID PARTICLES

The present invention relates to apparatus for generating aerosols of solid particles, particularly inhalable aerosols of vaccines and containers serving as syringues adaptable to these apparatus.

An apparatus according to the invention is composed, on the one hand, of a Micronizer or jet mill comprising a cylindrical chamber whose two axial ends are closed by two flat side walls, perpendicular to the axis of the chamber, one of which has an axial outlet conduit from the aerosol passing therethrough, into which chamber inlet nozzles for compressed gas open out tangentially and, on the other hand, means for introducing into this chamber a pulverulent product, which means comprise, on the one hand, one or more cavities, or revolution about an axis, which each communicate with the inside of said chamber via a channel which passes through one of said side walls and, on the other hand, one or more syringues, each constituted by a doser tube containing a determined dose of said pulverulent product and of which the front end is open and axially engaged, in sealed and easily removable manner, in one of said cavities, each syringue comprising a plunger which slides in each tube and the apparatus further comprising means for pushing said plungers.

One application of the aerosol generating apparatus according to the invention, to which particular reference will be made, is the production of inhalable aerosols of lyophilised microbes with a view to collectively vaccinating groups of men or animals, but the choice of this application does not of course limit the scope of the invention.

The production of microbe, bacteria or virus aerosols poses difficult problems in view of the fact that these micro-organisms are conserved in the lyophilised state in the form of very hydrophilic solid particles which tend to become entangled and to agglutinate.

On the other hand, for an inhalable vaccine to be effective, the particles suspended in the air must have dimensions smaller than 5 $\mu$ in order to penetrate deeply into the bronchi.

Moreover, the bigger the particles, the higher their speed of sedimentation, this reducing the probabilities of being inhaled and the effectiveness of the vaccine.

Experiments of collective vaccination by aerosols have shown that, to be effective, the aerosols must have a concentration of the order of 0.01 mg/l of particles of dimensions smaller than 5 $\mu$ and this concentration must remain constant for a sufficient length of time.

Generators of aerosols of solid particles comprising a jet mill, also designated under the proprietary name "Micronizer", are known, in which the lyophilised bacteria are introduced by a compressed air ejector. These generators have made it possible to produce aerosols of vaccines complying with the conditions of fineness of the particles in suspension but it is difficult accurately to determine the concentration, gradient of concentration and total dose of vaccine suspended in the air with these known apparatus, this constituting a serious default since this dose must be determined with very high precision otherwise accidents will occur, the consequence of which may be very serious, whether the inhaled dose be too week and the vaccination insufficient, or, on the contrary, the dose inhaled be too strong.

It is an object of the present invention to provide an aerosol generator apparatus and containers adaptable to these generators which make it possible accurately to determine the total dose of vaccine injected in a determined volume, e.g. in a poultry farm comprising a given number of heads of poultry, and to obtain an aerosol having a stable concentration for a sufficient period of time which is substantially uniform over the whole extent of the volume.

This object is achieved with the means used for introducing the vaccine or any other pulverulent product into the chamber of the jet mill.

These means are constituted on the one hand by one or more cavities, of revolution about an axis, which each communicate with the inside of the chamber of the mill by a channel which passes through one of the side walls of the chamber and, on the other hand, by one or more syringues, each composed of a doser tube, which contains a determined dose of a pulverulent product, the front end of which is open and is engaged axially, in sealed and easily removable manner, in one of said cavities, which tube comprises an axially mobile plunger and the apparatus comprises pushers which move said plungers.

The doser tubes adaptable to an apparatus according to the invention at the same time constitute disposable packages.

The result of the invention is a novel aerosol generator composed, in combination, of a jet mill and syringues containing a determined dose of a pulverulent product which are fitted into a cavity or socket opening directly into the chamber of the jet mill.

As each syringue contains a determined dose of solid particles, particularly of lyophilised vaccine, it is sufficient to proportionate this dose to the volume to be treated in order to be certain not to exceed a dangerous limit of concentration.

For example, to collectively vaccinate a certain number of head of poultry in premises of 55 $m^3$, a syringue is used which contains 5 g of lyophilised vaccine and one is certain not to exceed an average concentration of 0.01 mg/liter.

The doser tubes are prepared by the laboratory and delivered to the consumers ready to be fitted directly into the apparatus, after having removed the stoppers or capsules closing them, this avoiding any risk of error in dosage, any manipulation of the vaccine and any loss of vaccine in the circuits of the apparatus, and thus contributing to the precision of the dosage.

The fact that the syringues constitute disposable containers eliminates the problems of cleaning and the risks of mixing two different vaccines.

The means used for introducing the vaccine or any other pulverulent product in the chamber of the jet mill by means of syringues which are fitted into a cavity opening out directly into this chamber, enable all the pulverulent matter contained in the syringue to be introduced with certitude in the jet mill, since the space between the piston and the inlet orifice in the chamber of the mill is much reduced and all the matter located therein is driven into the mill by the air in motion which scavenges said space.

The containers containing a determined dose of vaccine or any other pulverulent product and constituting syringues adaptable to a generator according to the invention, constitute consumable, commercialisable products and the scope of the invention extends to these products.

The invention will be more readily understood on reading the following description with reference to the accompanying drawings, in which:

FIGS. 3 to 7 show vertical sections, on a larager scale, of the connection of the doser tube to the mill.

FIG. 8 shows a plan view of the notched ring of FIG. 6.

Figure 1:
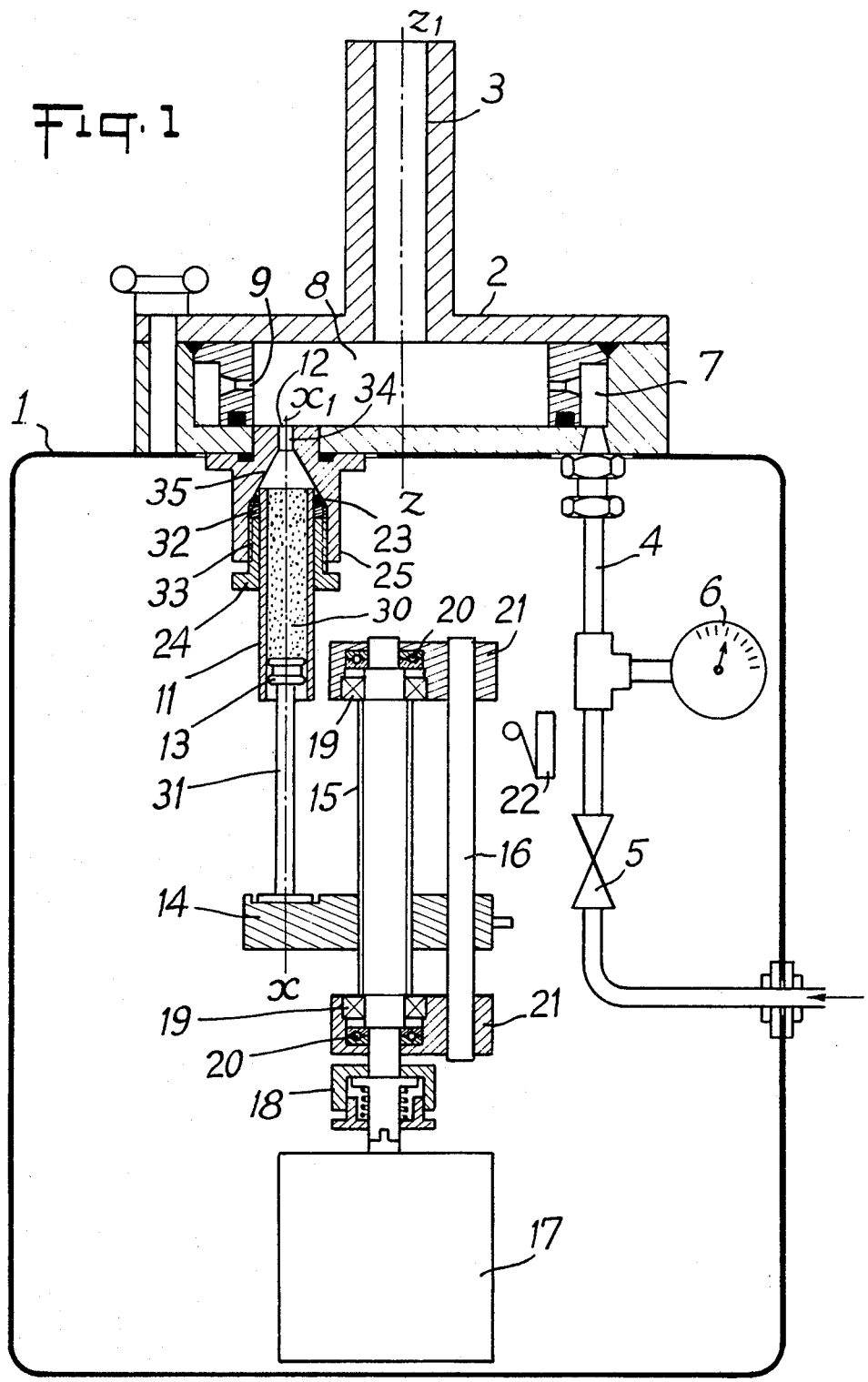
FIG. 1 shows a vertical section through an apparatus according to the invention.
Figure 2:
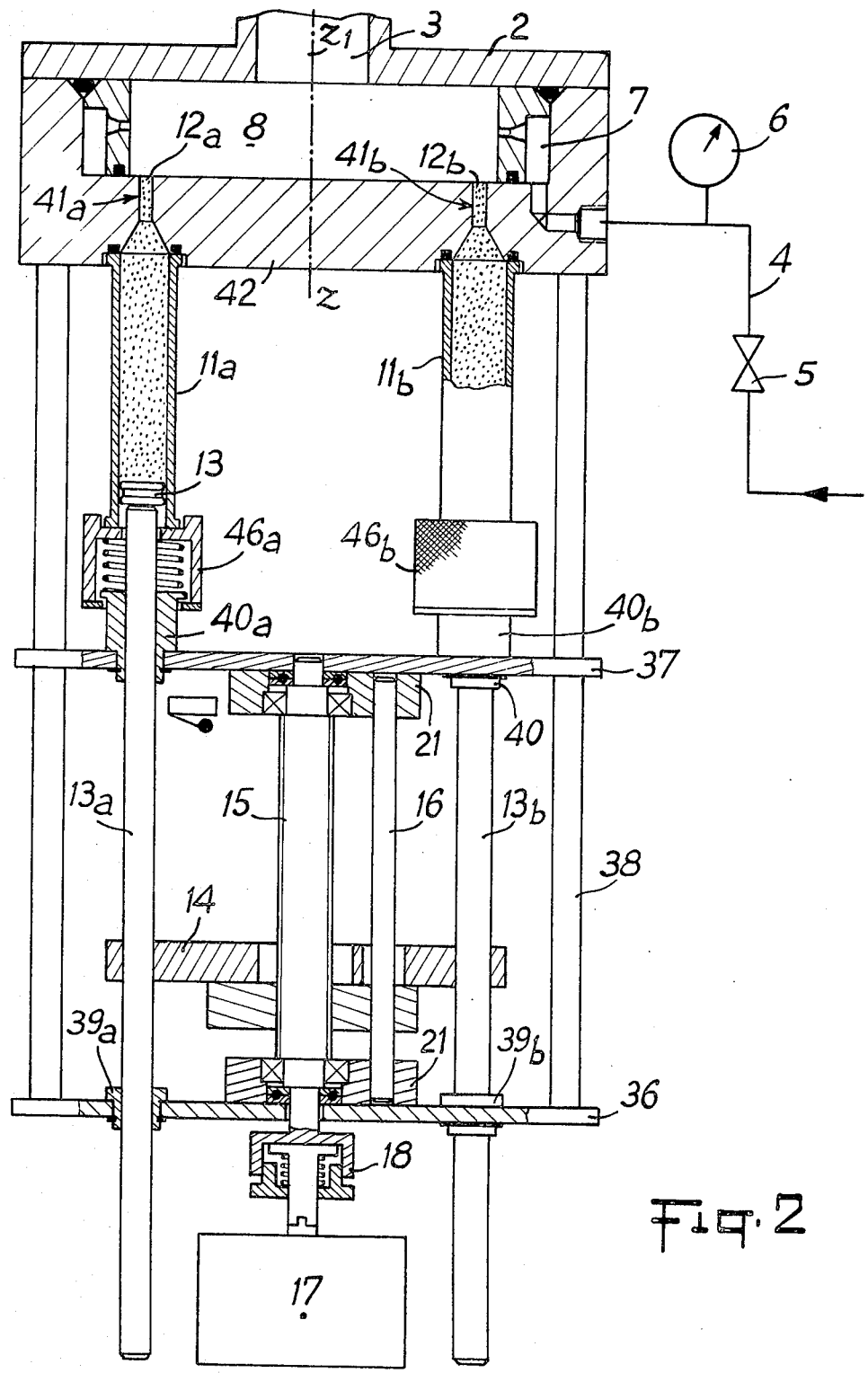
FIG. 2 shows a vertical section through another apparatus according to the invention.

Referring now to the drawings, the aerosol generator according to FIGS. 1 and 2 is composed of a casing 1 supporting a jet mill 2 also referred to as micronizer. This mill, with axis z-zl, is equipped with an axial conduit 3 through which a stream of air leaves, which is charged with solid, very finely ground particles, with dimensions of the order of a micron. This air, in which particles are suspended, constitutes an aerosol mist.

The jet mill 2 is fed with compressed air, under a pressure of for example 7 bars, through a conduit 4 comprising a valve 5 and a manometer 6. The compressed air arrives in an annular chamber 7 from which it passes into a central cylindrical chamber 8 through nozzles 9 having a more or less tangential orientation.

The bottom of the chamber 8 has one orifice 12 in the case of FIG. 1 or a plurality of orifices such as 12a, 12b, in the case of FIG. 2, through which a pulverulent product is introduced into the chamber 8 to be ground very finely and suspended in the air leaving the chamber.

In the case of FIG. 1, the means for feeding the mill are composed of a doser tube 11, of axis x-xl, containing a pulverulent product 30, for example a lyophilised vaccine.

A plunger 13 provided with a rod 31, slides in the tube 11.

The movement of the plunger pushes the vaccine 30 towards the orifice 12 and, insofar as the movement of the plunger is uniform, the flow of vaccine entering the mill is constant.

The doser tube 11 contains a determined dose of vaccine 30, for example 5 g, so that the quantity of vaccine suspended is accurately known. The tube 11 acts as a syringue comprising one or more outlet orifices 12 and enabling a determined quantity of product to be injected.

The tube 11 is, for example, a glass tube whose diameter remains constant with high precision over its whole length so that displacements of the plunger of equal length introduce into the mill equal volumes of product 30, whatever the position of the plunger.

The movement of plunger 13 is controlled by a mobile nut 14 driven in translation by a worm 15 of the micrometric screw type, on which it is screwed. The nut 14 is guided by a rod 16 which prevents it from rotating.

The worm 15 is rotated by a conventional variable-speed motor 17 by means of a torque limiting coupling sleeve 18. Ball bearings 19 and ball-thrust bearings 20 mounted in bearings 21 ensure the guiding and positioning of the worm 15. An end-of-stroke switch 22, actuated by nut 14, automatically stops the motor when the plunger 13 has come to the end of its upward stroke.

To return the nut into starting position, use may be made either of a nut, disconnectable from the worm, which is returned by hand, or a reversible motor 17.

The motor 17 and the worm 15 may possibly be replaced by a hydraulic or pneumatic device, for example, a jack.

The tube 11 is assembled in sealed and removable manner with the mill 2 and preferably constitutes a disposable container.

In the case of FIG. 1, a socket 25 is fixed in a bore passing right through the bottom of the chamber 8. The front end of the tube 11 is engaged in the socket 25 and held therein in sealed manner by means of a stuffing-box composed of an O-ring 23, a stuffing-box gland 24 which screws into the socket 25 and an intermediate ring 32. The socket 25 comprises a first cylindrical bore 33, of diameter greater than the outer diameter of the tube 11, which is internally threaded, on which the gland 24 is screwed.

It comprises a second bore 34, of diameter clearly smaller than the inner diameter of the doser tube, which opens out, through the orifice 12, into the chamber of the mill. These two bores, which are coaxial, are connected together by a convergent nozzle 35.

FIG. 3 shows on a larger scale the socket 25 and the front end of the tube 11 in this embodiment.

FIG. 2 shows an embodiment of an apparatus which differs from that of FIG. 1 in that it comprises a plurality of identical doser tubes 11a, 11b, etc . . . , distributed over the periphery of the chamber 8 and opening out into the bottom thereof through orifices 12a, 12b, etc . .

Each tube comprises its plunger 13, which is pushed by a rod 13a, 13b . . . The rods 13a, 13b, etc . . . are fast with a nut 14 mounted, as in the preceding example, on a central worm 15, rotated by a motor 17. The nut 14 is guided by a rod 16. The apparatus comprises two plates 36, 37 connected by cross-pieces 38. These plates support the bearings 21 and rod 16. The rods 13a and 13b slide through rings 39a, 39b and 40a, 40b.

In this example, channels 41a, 41b . . . are made through the bottom 42 of the chamber 8 and open out thereinto through orifices 12a, 12b.

FIG. 7 shows, on a larger scale, that part of the apparatus.

The channels 41 comprise a first convergent section 43 having an external diameter substantially equal to the diameter of the doser tube 11, followed by a second co-axial cylindrical channel 44, having a diameter clearly smaller than the diameter of the tube 11. The front end of the tube 11 is an abutment against an O-ring 45 which ensures the seal of the contact.

The rear end of the tube 11 is pushed by an elastic device 46 composed of a hollow ring 47 inside which is housed a spring 48 resting on a ring 40. A washer 49 is fixed to the end of the ring 47 and is engaged behind a shoulder 50 of the ring 40 to hold the device 46 on the ring 40.

FIG. 4 shows an embodiment of the fixation of the doser tube 11 on the jet mill 2 by means of a threaded socket 25. This embodiment differs from that of FIG. 3 by the fact that the diameter of the first bore 33a. on which is screwed the gland 24a, is clearly greater than the outer diameter of the tube 11 so that a lining 51 extending the ring 32a, is introduced between the tube and the gland 24a. This example illustrates how doser tubes 11 of different diameters may be mounted on the same socket by using diameter adapters.

FIG. 5 shows another embodiment of the fixation of the tube 11 on the bottom of the jet mill 2. In this example, a bore 52 is pierced in the bottom of the chamber of the jet mill and opens thereinto through an orifice 12 of smaller diameter. The front end of the tube 11 is engaged in the bore 52 and held in abutment against the bottom thereof by a stuffing box composed of a seal 53, a gland 54 and a conical-sided ring 55. The gland 54 is screwed onto a threaded socket 56 fixed around the bore. A member 61 pierced with a channel 62, convergent then cylindrical, connects the internal diameter of the tube to the orifice 12. This member is inserted into the tube 11, behind a shoulder 63.

FIGS. 6 and 8 show another embodiment of the assembly between the doser tube and the mill which is similar to the one shown in FIG. 7. The front face of the doser tube 11 is maintained in sealed abutment against seal 45 by means of a notched ring 57 threaded on the tube and held applied against an outer shoulder 58 of the end of the tube, by springs 59 which are compressed by means of screws 60 screwed in the bottom of the mill. FIG. 8 shows a plan view of the ring 57 showing the notch 61 whose width is slightly greater than the outer diameter of the tube 11.

FIGS. 3 to 8 illustrate several embodiments of the removable fixation of the doser tube on the mill.

These examples are not limiting.

In all these embodiments, the orifice 12, which opens out into the mill, has a diameter clearly smaller than the diameter of the tube 11, to avoid the pulverulent product which is located at the front end of the tube, from being taken along by the air in motion coming from the mill. For example, if the tube 11 has an internal diameter of 12 mm, the orifice 12 will have a diameter of 6 mm.

A truncated surface makes it possible to connect the cylindrical body of the tube to the orifice 12.

FIGS. 9 to 14 show embodiments of doser tubes.

These tubes are composed of a cylindrical container 11, containing a determined dose of a powder product 30, for example a dose of vaccine constituted by lyophilised microbes. This container is closed in sealed manner, at its two ends, by removable stoppers and constitutes a syringe adaptable to an apparatus according to the invention and a disposable packing, to be thrown away after use.

Figure 9:
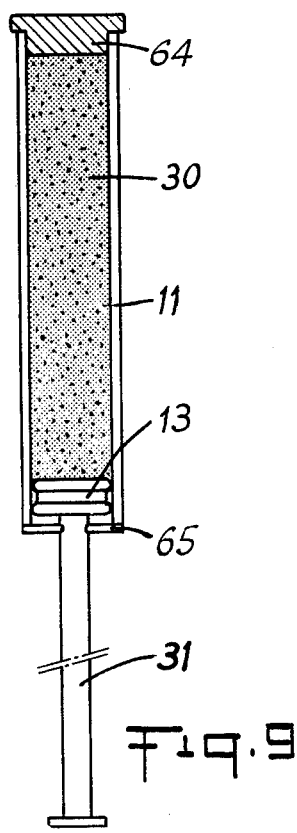
FIGS. 9 to 14 are sections through containers according to the invention.

In the example of FIG. 9, the front end of the tube is closed by a stopper 64 and the rear end is closed by a piston 13 fast with a rod 31 which forms part of the syringe. A split ring 65, forming a circlip, is engaged in a groove of the rod 31 and comes into abutment against the end of the tube 11.

Figure 10:
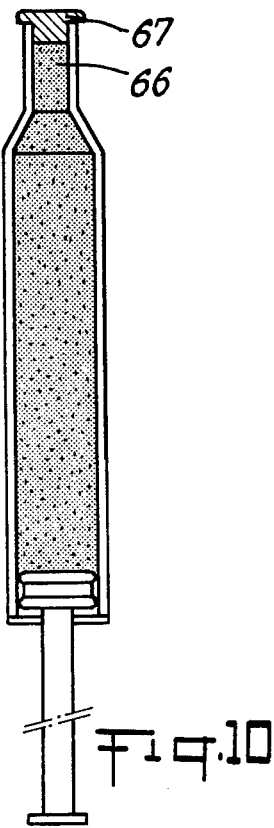

FIG. 10 shows a variant embodiment in which the front end of the tube 11 comprises a cylindrical neck 66 closed by a removable stopper 67. This syringue is adapted to a fixation according to FIG. 5.

Figure 11:
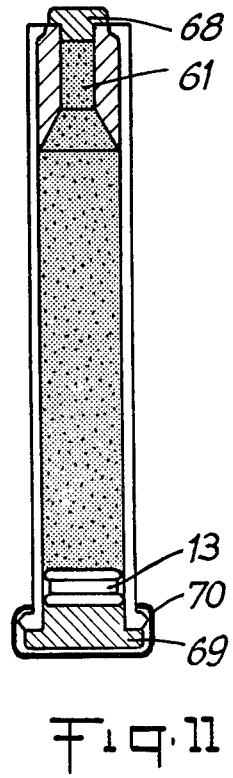

FIG. 11 shows a variant container adaptable to a fixation according to FIG. 5 which contains, at the front end, a hollow member 61, inserted into the container and obturated by a removable stopper 68. This container contains, at the rear end, a piston 13, engaged in the container and it is closed by a second stopper 69 held in place by a crimped, tear-away capsule 70.

Figure 12:
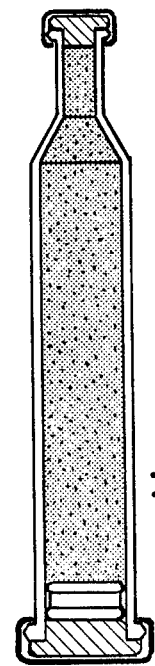

The variant container shown in FIG. 12 has a front end identical to the one of FIG. 10 and a rear end identical to that of FIG. 11.

Figure 13:
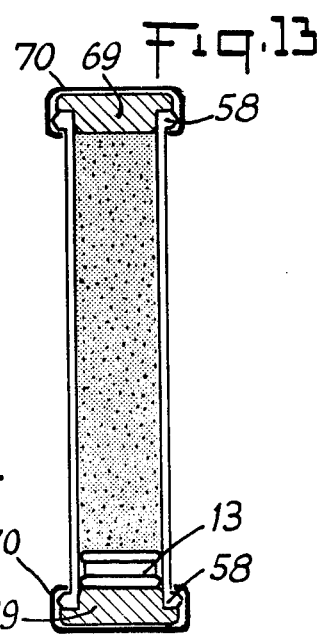
Figure 14:
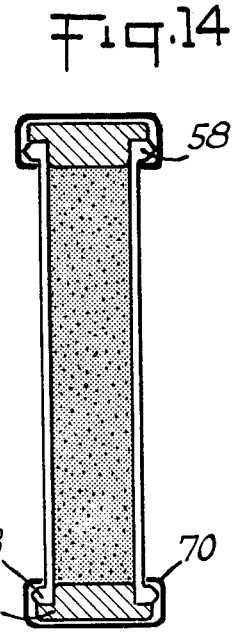

FIGS. 13 and 14 show containers adaptable to fixations according to FIGS. 6 and 7. These containers comprise, at their two ends, a peripheral rib 58 forming a shoulder. The ends are closed by means of a stopper 69 held by a crimped capsule 70. The container according to FIG. 13 is delivered with a plunger 13 whilst the one of FIG. 14 is delivered without plunger.

For vaccines, the containers delivered with a plunger, with or without push rod, are preferred embodiments since they avoid any contact between the vaccine and any member of the apparatus belonging to the push-mechanism.

What I claim is:

1. An apparatus for generating aerosols of solid particles, particularly inhalable aerosols of vaccines, comprising, a micronizer having a cylindrical chamber formed therein, said micronizer having a pair of opposed axial ends by first first and second flat end walls located perpendicular to the longitudinal axis of the chamber and closing the ends of the chamber, one of said first end walls having an axial outlet formed therein to permit aerosol in said chamber to pass therethrough; and a peripheral side wall extending between said end walls, said side wall and said end walls defining said chamber therebetween; said side wall including a plurality of inlet nozzles for compressed gas opening tangential to said longitudinal axis into said chamber; means for introducing compressed gas into said nozzles; means for introducing a determined dose of a pulverulent product, said introducing means comprising, at least one cavity formed in one of said end walls the second of said end walls and radially disposed from said longitudinal axis and communicating with the inside of said chamber through a conduit formed in the second end wall, a syringe associated with said cavity comprising a doser tube containing a determined dose of said pulverulent product, said tube having opposite opened front and rear ends with said front end being axially engaged in its associated cavity; means for removably securing and sealing said open front end of the doser tube within the cavity in which it is engaged; and means for introducing and pushing substantially all of the pulverulent product in said syringe into said chamber through said channel; said pushing means including a plunger slidably positioned in said doser tube and means for pushing said plunger from the rear end of the tube towards the forward open end to urge pulverulent product in the tube through said channel.

2. An apparatus as claimed in claim 1, wherein the means for pushing the plunger comprises a worm gear extending generally parallel to the axis of said chamber, a variable speed motor for rotating said worm gear; a nut threadedly engaged with said worm gear; at least one fixed guide rod extending through said nut, parallel to said worm gear, and a pusher rod located between the nut and said plunger in the syringe whereby, said nut moves in translation along the worm gear when the worm gear is rotated and simultaneously pushes said plunger through said push rod intercalated between said nut and said plunger.

3. Apparatus as claimed in claim 1, wherein said cavity has the form of a truncated funnel whose wider base is on the side of the second end wall opposite the chamber and receives the front end of the doser tube; said wider base having a greater diameter than the diameter of said doser tube, said funnel shaped cavity being extended from its narrower base by said conduit which comprises a coaxial cylindrical channel which passes through the second end wall in which the cavity is formed and which opens inside the chamber, said channel having a diameter smaller than the inner diameter of said doser tube.

4. Apparatus as claimed in claim 3, wherein said cavity comprises a truncated channel whose axis is parallel to the axis of the chamber and which converges to the side of the second end wall away from said chamber through a part of the thickness of said second end wall, followed by a coaxial cylindrical channel which passes through said second wall and which opens out into the chamber, the front of said doser tube being secured in sealed relation adjacent the outer orifice of said truncated channel.

5. An apparatus as claimed in claim 4, wherein the front end of said doser tube includes an outwardly projecting peripheral flange; and a notched ring fitted around said tube in abutment against said flange; a plurality of screws extending through said ring into threaded engagement with said one end wall; and a plurality of springs respectively surrounding and compressed by said screw to hold the ring against the flange.

6. An apparatus as claimed in claim 4, wherein the rear end of said doser tube includes an elastic pusher thereon having an axial orifice through which said pusher rod is inserted to act on the plunger.

7. An apparatus as claimed in claim 1, wherein said cavity comprises a female socket secured in a bore passing through said second end wall of the chamber and the front end of the doser tube is secured into said socket and is maintained in sealed manner therein by a stuffing box.

8. Apparatus as claimed in claim 7, wherein said socket has inner and outer ends and has at its outer end a first bore of a diameter greater than the outer diameter of said doser tube; said tube having, over a part of its length, a female threading formed thereon; said stuffing box including a nut which is screwed onto said tube; the inner end of said socket having a second bore whose diameter is smaller than the inner diameter of said doser tube and which opens into said chamber; said socket including, between said first and second bores, a convergent channel which connects the bores and which receives the front end of said doser tube; and a seal in said socket around said front end of the doser tube.

9. An apparatus as claimed in claim 1, wherein said cavity comprises a bore extending parallel to the axis of the chamber, said bore having a first section through a part of the thickness of said second wall whose diameter is slightly greater than the outer diameter of said doser tube and a second section which is coaxial with the first section, but of smaller diameter, which passes through said end wall and opens into said chamber; the front end of the doser tube being engaged in said first bore section in sealed relation thereto.

10. An apparatus as claimed in claim 1, wherein said syringe comprises a disposable container having a cylindrical tube containing a determined dose of pulverulent lyophilized vaccine, having opposed front and rear open ends and removable stoppers for hermetically sealing said ends.

11. An apparatus claimed in claim 10, wherein said container includes a plunger inserted into said tube at the rear end.

12. An apparatus as claimed in claim 10, wherein the front end of said container comprises a cylindrical neck, coaxial with said tube and connected thereto by a truncated channel.

13. An apparatus as claimed in claim 10, wherein said container includes a hollow ring having a cylindrical channel formed therein inserted in the front end of said tube, said channel having a diameter smaller than that of the tube, said channel being extended at its rear end within the tube by a truncated channel section which connects it to the walls of said tube.

14. An apparatus as claimed in claim 10, wherein said container comprises a cylindrical tube whose front and rear end have an outwardly projecting flange formed thereon.

15. An apparatus as defined in claim 1 including a plurality of said cavities formed in said second end wall and a plurality of syringes respectively associated with said cavities for supplying said pulverulent material to said chamber.

* * * * *